(12) United States Patent
Berger et al.

(10) Patent No.: US 7,605,287 B2
(45) Date of Patent: Oct. 20, 2009

(54) POLYALKYLATED ARYLALKYL SULFONIC ACIDS AND THEIR SALTS

(75) Inventors: Paul Daniel Berger, Sugar Land, TX (US); Christie Huimin Berger, Sugar Land, TX (US); Guohua Cao, Missouri City, TX (US); Oliver Yehung Hsu, Missouri City, TX (US)

(73) Assignee: Oil Chem Technologies, Sugar Land, TX (US)

( * ) Notice: Subject to any disclaimer, the term of this patent is extended or adjusted under 35 U.S.C. 154(b) by 67 days.

(21) Appl. No.: 11/895,497

(22) Filed: Aug. 24, 2007

(65) Prior Publication Data

US 2009/0023951 A1    Jan. 22, 2009

Related U.S. Application Data

(60) Provisional application No. 60/959,943, filed on Jul. 18, 2007.

(51) Int. Cl.
  *C07C 303/22*    (2006.01)
(52) U.S. Cl. .................................................... 562/115
(58) Field of Classification Search ................ 562/115
  See application file for complete search history.

(56) References Cited

U.S. PATENT DOCUMENTS

| | | | |
|---|---|---|---|
| 3,337,615 A * | 8/1967 | Roberts et al. .............. | 562/115 |
| 4,004,638 A | 1/1977 | Burdyn et al. | |
| 4,139,498 A * | 2/1979 | Kawakami et al. .......... | 510/537 |
| 4,220,204 A | 9/1980 | Hughes et al. | |
| 4,536,301 A | 8/1985 | Malloy et al. | |
| 6,022,834 A | 2/2000 | Hsu et al. | |
| 6,043,391 A | 3/2000 | Berger et al. | |
| 7,256,306 B2 | 8/2007 | Dado et al. | |
| 2004/0242920 A1* | 12/2004 | Dado et al. .................. | 562/41 |

FOREIGN PATENT DOCUMENTS

GB    2232428    6/1989

OTHER PUBLICATIONS

Jiang et al, Synthesis of Unsymmetrical Bolaform Surfactants With a Sulfonate Group and a Carboxyl Group, J. Surfact Deterg (2007) 10: 131-136 Springer N.Y.

* cited by examiner

*Primary Examiner*—Peter G O'Sullivan

(57) ABSTRACT

The present invention discloses a process for producing polyalkylated arylalkyl sulfonic acids by reacting arylalkyl sulfonic acids with olefins. The polyalkylated arylalkyl sulfonic acids may be further neutralized with alkalis or amines to form the corresponding sulfonated salts. The present invention also makes possible manufacture of polyalkylated arylalkyl sulfonic acids as first intent products using an inexpensive and simple reaction. The structure of the polyalkylated arylalkyl sulfonic acids produced using the process described in the present invention is shown below:

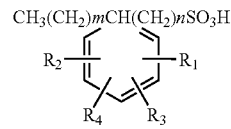

Where
$R_1$, $R_2$ and $R_3$ are each separately and independently H, alkyl (branched or linear C1 to C30), $(-CH_2CH_2O)_a$, $(-CH(CH_3)CH_2O)_b$, or $(-CH_2CH_2O)_c(-CH_2(CH_3)CH_2O)_d$,
m+n=8 to 28
$R_4=CH_2CH_3$, $CH_2CH_3Y$ or $Y(CH_2)_pCH(CH_2)_qY$
p+q=0 to 27
a=1 to 30
b=1 to 30
c+d=2 to 30
$Y=CH_3$, COOH, $CH_2OH$, $CH_2(-CH_2CH_2O)_a$, $CH_2(-CH(CH_3)CH_2O)_b$, $CH_2(-CH_2CH_2O)_c(-CH_2(CH_3)CH_2O)_d$, aromatic, or substituted aromatic.

13 Claims, No Drawings

POLYALKYLATED ARYLALKYL SULFONIC ACIDS AND THEIR SALTS

CROSS REFERENCE TO RELATED APPLICATIONS

This application is based on provisional patent application Ser. No. 60/959,943 filed on Jul. 18, 2007.

FIELD OF THE INVENTION

The present invention relates to a process for producing higher molecular weight anionic surfactants. More particularly the present invention relates to a process for preparing dialkyl and higher substituted aromatic sulfonic acids and sulfonates using arylalkyl sulfonic acids and olefins.

The new process of the present invention for preparing the higher molecular weight poly substituted arylalkyl sulfonic acids and sulfonates, commonly known as heavy arylalkyl sulfonic acids and heavy arylalkyl sulfonates, has the following advantages over existing processes:

1. Di and higher substituted arylalkyl sulfonic acids and sulfonates can be produced easily in high yields as a first intent product.
2. Di and higher substituted arylalkyl sulfonic acid and sulfonates can be produced without using the costly, conventional alkylation processes.
3. Di and higher substituted arylalkyl sulfonic acid and sulfonates can be produced without using the conventional costly and hazardous catalyst such as aluminum chloride ($AlCl_3$) or hydrofluoric acid (HF).
4. The Di and higher substituted arylalkyl sulfonic acids and sulfonates have superior solubility characteristics and lower viscosities than their existing counterparts.
5. The process produces high molecular weight polyalkylated sulfonic acid without the necessity of sulfonated high molecular weight, viscous alkylates.
6. Di and higher substituted arylalkyl sulfonic acids and their salts can be produced containing carboxylate, alcohol, aromatic, and substituted aromatic groups.
7. Di and higher substituted arylalkyl sulfonic acids and their salts can be produced from a minimum number of raw materials at low cost and high yield.

THE PRIOR ART

Alkyl benzene sulfonates, a member of the alkylaryl sulfonate family of surfactants have been popular surfactants for a wide variety of detergent and industrial use. Beginning just after World War II, synthetic detergents based on the reaction of propylene tetramer and benzene using $AlCl_3$ catalyst began to gain popularity and widespread use as laundry detergents. During the 1960s alkylbenzene sulfonates based on branched alkyl groups were found to be causing excessive foaming in sewage treatment plants and in rivers and lakes due to their slow biodegradability. Linear alkylbenzenes based on the reaction of linear olefins (U.S. Pat. No. 3,585,253 issued to Huang on Jun. 15, 1971) or linear chloroparaffins (U.S. Pat. No. 3,355,508 issued to Moulden on Nov. 28, 1967) were developed which gave acceptable detergency and were quickly biodegraded. Even more recently, the $AlCl_3$ process has been replaced by the HF process and the Detal Process because of environmental objections to the $AlCl_3$ process. Table 1 shows the typical yields obtained for detergent alkylates and heavy alkylate using HF catalyst.

TABLE 1

Typical Yields of Detergent Alkylate and Heavy Alkylate (values in tons)

| | Branched Alkylate | Linear Alkylate |
|---|---|---|
| Material Charged | | |
| Linear Paraffins | — | 82.9 |
| Benzene | 39.9 | 34.3 |
| Propylene tetramer | 86.7 | — |
| Total charged | 126.6 | 117.3 |
| Materials Produced | | |
| Hydrogen | — | 1.1 |
| Light ends | — | 3.8 |
| HF regenerator bottoms | 2.5 | 2.8 |
| Light alkylate | 8.0 | — |
| Detergent alkylate | 100.0 | 100.0 |
| Heavy alkylate | 16.1 | 9.6 |
| Total produced | 126.6 | 117.3 |

Conventional processes are designed to optimize the yields of detergent alkylate (predominantly monoalkylbenzene). The yields of heavy alkylate (predominantly polyalkylbenzene) are therefore low, and in general are available only from about 0.5 to about 10% of the total alkyl benzene production. These heavy alkylates however find considerable demand as oil soluble surfactants and specialty chemicals. Dialkylbenzene sulfonates (U.S. Pat. No. 4,004,638 issued to Burdyn, Chang and Cook on Jan. 25, 1977, U.S. Pat. No. 4,536,301 issued to Malloy and Swedo on Aug. 20, 1985), alkyl xylene sulfonates (EP121964) and dialkyl phenol polyethoxylated alkyl sulfonates (U.S. Pat. No. 4,220,204 issued to Hughes, Kudchadker and Dunn on Sep. 2, 1980) have all been used to increase the productivity of crude oil; however; the availability of these materials has been limited because of the low yields of heavy alkylates available for conversion to their corresponding sulfonates. U.S. Pat. No. 6,043,391 issued to Berger, et al on Mar. 28, 2000 describes a process of producing polyalkylated aromatic sulfonic acids by reacting benzene or an alkylated benzene with an AOS acid. U.S. Pat. No. 7,256,306 issued to Dado and Bernhardt on Aug. 14, 2007 also alludes to the manufacture of heavy alkylate aromatic sulfonates by reacting benzene or an alkylated benzene with AOS acid. However, there are no effective and economical commercially feasible process available, until this invention, for producing polyalkylated arylalkyl sulfonic acids and their sulfonates as a first intent product.

U.S. Pat. No. 6,022,834 issued Feb. 8, 2000 to Hsu and Hsu describes the use of high molecular weight alkylbenzene sulfonates in combination with linear or branched lower molecular weight as components for formulation used for the recovery of crude oil from subterranean reservoirs. U.S. Pat. No. 6,043,391 also discloses the use of high molecular weight poly-substituted alkyl benzene sulfonates obtained from the high molecular weight co-product from the alkylation of benzene. These poly-substituted benzene sulfonic acids are used along with lower molecular weigh arylalkyl sulfonic acids to form useful compositions for the recovery of oil from subterranean reservoirs.

Mixtures of natural and synthetic alkylaryl sulfonates are used to provide ultra-low interfacial tensions ($<1.0\times10^{-2}$ mN/m) when used in combination with various alkali materials such as NaOH or $Na_2CO_3$ and contacted with crude oil. For example, U.S. Pat. No. 4,536,301 issued to Malloy and Swedo on Aug. 20, 1985 uses mixtures of mono and dialkylbenzene sulfonates to obtain ultra-low interfacial tensions against crude oil, U.S. Pat. No. 4,004,638 issued to Burdyn, Chang and Cook on Jan. 25, 1977 uses similar mixtures along with alkali agent to obtain ultra-low IFT and GB 2,232,428 filed by Muijs, Beers, and Roefs on Jun. 6, 1989, uses mixtures of dialkylbenzene alkali sulfonates and polyalkoxyphenyl-ether alkali sulfonates also to obtain low IFT values. All these references claim increased oil recovery by injection of the sulfonate mixtures into subterranean crude oil reservoirs.

Jiang, et al J. Surfact Deterg (2007) 10:131 131-136, describe a method for synthesizing boloform surfactants by alkylating an aromatic with a substituted olefin such as a carboxylic acid using a catalyst and then sulfonating the aromatic ring with sulfur trioxide. The process of the present invention offers a much simpler and effective method to synthesize these products as well as producing products with structures having better surface properties and solubility since the sulfonate group is on the alkyl chain and not the aromatic ring.

SUMMARY OF INVENTION

The present invention resides in an improved process for producing polyalkylated arylalkyl sulfonic acids and their sulfonates where the aromatic group is first sulfonated and alkylated, then the resulting arylalkyl sulfonic acid is further reacted with one or more olefin to form a higher molecular weight polyalkylated arylalkyl sulfonic acid. This higher molecular weight polyalkylated arylalkyl sulfonic acid can be further reacted with alkalis including but not limited to sodium hydroxide, sodium carbonate, potassium hydroxide, potassium carbonate, calcium hydroxide, magnesium hydroxide, or amines to form their corresponding sulfonate salts.

DETAILED DESCRIPTION OF THE INVENTION

The present invention uses alpha olefin sulfonic acid produced by the thin film sulfonation of an alpha-olefin to alkylate an aromatic compound including, but not limited to benzene, naphthalene, or a substituted aromatic compound including, but not limited to, toluene, xylene, ethyl benzene to produce the corresponding aryl alkyl sulfonic acid having an additional alkyl group derived from the alpha-olefin used during the reaction. The structures of these arylalkyl sulfonic acids are disclosed in U.S. Pat. No. 6,043,391. A catalyst has been found useful to reduce the reaction temperature, the reaction times and improve yields. Useful catalysts include strong acids, including but not limited to $H_2SO_4$, methane sulfonic acid, sulfosuccinic acid, alkylaryl sulfonic acids, arylalkyl sulfonic acids including the reaction product itself, and other strong acid catalysts generally used for alkylation. The catalyst is used at concentrations below 25% of the initial amount of alpha olefin sulfonic acid, usually from 1 to 20%. The exact amount of catalyst used depends on the AOS acid, the aromatic, and the temperature used. Higher temperatures, up to the decomposition temperatures of the reactants are preferred. Pressure may be necessary to reach the desired higher temperatures when using low boiling starting materials such as benzene. The subsequent arylalkyl sulfonic acid is then reacted with one or more olefin to form a polyalkylated arylalkyl sulfonic acid. Unexpectedly we have found that the use of sulfonated arylalkyl sulfonic acids allows the olefin to easily attach itself to the aromatic ring of the arylalkyl sulfonic acid resulting in high yields of poly arylalkyl sulfonic acids and very little unreacted olefin. This is in contrast to the results obtained when a conventional alkylaryl sulfonic acid such as alkylbenzene sulfonic acid is combined with an olefin. In this case no reaction was observed.

The present invention involves a process for the manufacture of polyalkylated arylalkyl sulfonic acids and their sulfonates comprising: reacting a sulfonated aryl alkyl compound with an olefin. The sulfonated arylalkyl compound has the structure below:

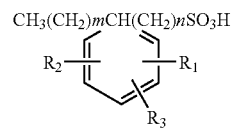

Where:
$R_1$, $R_2$ and $R_3$ are each separately and independently H, alkyl (branched or linear C1 to C30), $(-CH_2CH_2O)_a$, $(-CH(CH_3)CH_2O)_b$, or $(-CH_2CH_2O)_c(-CH_2(CH_3)CH_2O)_d$,
m+n=8 to 28
a=1 to 30
b=1 to 30
c+d=2 to 30

The resulting polyalkylated arylalkyl sulfonic acid after the reaction with olefin has the structure below:

Where:
$R_1$, $R_2$ and $R_3$ are each separately and independently H, alkyl (branched or linear C1 to C30), $(-CH_2CH_2O)_aH$, $(-CH(CH_3)CH_2O)_bH$, or $(-CH_2CH_2O)_c(-CH_{2(CH3)}(CH_2O)_dH$;
m+n=8 to 28
a=1 to 30
b=1 to 30
c+d=2 to 30
$R_4=CH_2CH_3$, $CH_2CH_2Y$ or $Y(CH_2)_pCH(CH_2)_qY$
$Y=CH_3$, COOH, $CH_2OH$, $CH_2(-CH_2CH_2O)_a$, $CH_2(-CH(CH_3)CH_2O)_a$, $CH_2$ $(-CH_2CH_2O)_c(-CH_2(CH_3)CH_2O)_d$, aromatic, or substituted aromatic.
p+q=0 to 27

Olefins may be linear or branched and from C2 to C30 carbons in length. Alpha-olefins (AO) as well as internal olefins (IO) may be used. The olefins may also contain other substituents including, but not limited to, alkenyl aromatics, unsaturated alcohols, or unsaturated carboxylic acids example but not limited to styrene, oleyl alcohol, oleic acid. The olefins may be terminated at one or more ends with benzene or substituted aromatics, carboxylate groups or alcohol groups. Mixtures of more than one olefin may be used. Using the present process and unsaturated alcohols and acids as the olefin produces boloform surfactants having unique structures and properties. The unsaturated acids and alcohol derivatives may be neutralized and further reacted with ethylene oxide, propylene oxide, butylenes oxide or mixtures of these oxides to form ether sulfates and ether sulfonates.

This reaction is carried out at temperatures between 40° C. and 200° C., preferably between 80° C. and 140° C., using approximately equimolar amounts of olefin and arylalkyl sulfonic acid. If very volatile or gaseous olefins are used the process may be carried out at elevated pressures.

During the reaction, the olefin is slowly added to the arylalkyl sulfonic acid at the reaction temperature. The uniqueness of the reaction is that the starting arylalkyl sulfonic acids serves as the catalyst as well as one of the reactants for the formation of the polyalkylated arylalkyl sulfonic acid. Without being bound by any particular theory we believe that the presence of the sulfonic acid group at the end of the alkyl chain strongly activates unoccupied positions on the ring making them amenable to addition by unsaturated compounds such as olefins.

The polyalkylated arylalkyl sulfonic acid can be further neutralized with alkalis to make the salts of the polyalkylated arylalkyl sulfonic acid, including but not limited to sodium hydroxide, sodium carbonate, potassium hydroxide, potassium carbonate, calcium hydroxide, magnesium hydroxide, ammonium hydroxide, or amines to form their corresponding sulfonate salts.

The polyalkylated arylalkyl sulfonic acids and their salts have been found useful as surfactants for many applications including, but not limited to, heavy duty cleaning, oil recovery, metal treating and cutting fluids. The products can be combined with other surfactants to form useful synergistic mixtures.

The process of the present invention for making polyalkylated arylalkyl sulfonic acids offers many unique advantages over the existing processes for manufacturing polyalkylaromatic sulfonic acids and their sulfonates. (1) Useful polyalkyl arylalkyl sulfonic acids and their sulfonates of different molecular weights can be made easily and economically as first intent products. (2) The starting reactant arylalkyl sulfonic acid is also an effective catalyst so additional catalyst is not required. (3) The polyalkylated arylalkyl sulfonic acid is made by alkylating the arylalkyl sulfonic acid with olefin and the process does not require the heavy alkylaromatic (heavy alkylate) precursor to be sulfonated. (4) As is know to those familiar with the art, the thin film sulfonation process used to sulfonate alkylates is limited to lower viscosity and low molecular weight alkylates. Higher viscosity an/or higher molecular weight alkylates may cause poor conversion, plugging and fouling of the sulfonation equipment. The process of this invention uses the thin film sulfonation unit to produce the low molecular weight, low viscosity olefin sulfonic acid, which are further processed outside the sulfonation unit to form the final products. (5) The process of the present invention does not require the conventional expensive alkylation process and catalyst or the use of any alkylate starting material since the arylalkyl sulfonate uses only olefin, an aromatic compound, and sulfur trioxide and the final product only requires additional olefin. This eliminates the cost of building and maintaining an alkylation plant to produce alkylate. This also eliminates the need for toxic and expensive catalysts such as aluminum chloride or hydrofluoric acid that are used in such plants.

EXAMPLE 1

86.2 grams (0.2 Mole) of 1:1 mixture by weight of 1-tetradecanesulfonic acid, (dimethylphenyl)- (common name XSA-14™) and 1-hexadecanesulfonic acid, (dimethylphenyl)- (common Name XSA-16™) was added to a three-necked round bottom flask. XSA-14 and XSA16 are produced by Oil Chem Technologies, Inc. The material was heated to 130° C. at which time 196 grams (0.2) moles of 1-tetradecene were added dropwise over a 1.5 hour period. The material was allowed to react and additional 3.5 hours at 130° C. after which it was analyzed for residual 1-tetradecene by Gas Liquid Chromatography and for anionic activity by CID two-phase titration. Residual tetradecene was found to be 2.4% by weight and anionic activity 97.6% by weight. This material was used to formulate an oil recovery surfactant as described in Example 10 to follow.

EXAMPLE 2

86.2 grams (0.2 Mole) of 1:1 mixture by weight of 1-tetradecanesulfonic acid, (dimethylphenyl)- and 1-hexadecanesulfonic acid, (dimethylphenyl)- was added to a three necked round bottom flask. The material was heated to 130° C. at which time 32.2 grams (0.2) moles of Neodene™ 1112, a C11-C12 internal olefin produced by Shell Chemical was added dropwise over a 15 minute period. The material was allowed to react and additional 4 hours at 130° C. after which it was analyzed for residual 1-tetradecene by Gas Liquid Chromatography and anionic activity by CID two-phase titration. Residual tetradecene was found to be 1.5% by weight and anionic activity 98.3% by weight.

EXAMPLES 3-9

The following examples on Table 2 show the reactants used and yields obtained using the method employed in Examples 1 and 2 for several other reactions carried out with different starting materials included within the scope of the present invention. In the case of propylene, the reaction was carried out under pressure in a 2-liter stainless steel Paar reactor. In all cases equimolar mixtures of the two reactants were used.

TABLE 2

Polyalkylated Aryl Alkyl Sulfonic Acids Prepared Using the Process of the Present Invention

| Example # | Arylalkyl Sulfonic acid | Olefin | Reaction Temp, °C. | Reaction Time, hr | Residual Olefin, % by wt | Anionic Activity, % by wt |
|---|---|---|---|---|---|---|
| 1 | XSA-1416 ™ | C14 AO | 130 | 5 | 1.2 | 97.6 |
| 2 | XSA-1416 ™ | C11-12 IO | 130 | 5 | 1.5 | 98.3 |
| 3 | XSA-1416 ™ | C3 | 80 | 2 | 0.8 | 98.2 |
| 4 | XSA-14 ™ | C6 AO | 120 | 3 | 1.1 | 98.8 |
| 5 | XSA-14 ™ | C12 AO | 130 | 5 | 0.72 | 98.9 |
| 6 | XSA-16 ™ | C16 IO | 130 | 5 | 0.76 | 98.1 |
| 7 | XSA-18 ™ | C18 AO | 130 | 6 | 2.1 | 97.2 |
| 8 | XSA-2024 ™ | C12 AO | 130 | 6 | 4.2 | 95.1 |
| 9 | XSA-1416 ™ | C1416 AO | 130 | 5 | 1.9 | 97.9 |

Note:
XSA-14 ™: 1-tetradecanesulfonic acid, (dimethylphenyl)-
XSA-16 ™: 1-hexadecanesulfonic acid, (dimethylphenyl)-
XSA-1416 ™: 1-tetradecanesulfonic acid, (dimethylphenyl)-; 1-hexadecanesulfonic acid, (dimethylphenyl)-1:1 ratio
XSA-18 ™: 1-octadecanesulfonic acid, (dimethylphenyl)-
XSA-2024 ™: 1-eicosanesulfonic acid, (dimethylphenyl)-; 1-docosane sulfonic acid, (dimethylphenyl)- and 1-tetracosanesulfonic acid, (dimethylphenyl)-

EXAMPLE 10

This example shows the utility of the polyalkylated aryl alkyl sulfonates in formulations used to recover crude oil. The commercially available heavy alkylate sulfonates is used as comparison to show the effectiveness of the products prepared using the present invention. The importance here is that these products can be tailor-made in large quantities necessary for full-scale field applications. The utility of the products of the invention as surfactants for Alkaline Surfactant Polymer (ASP) Flooding was evaluated in the examples using surfactant c formulations as listed below.

Formulation A
17.0 g Isopropanol
5.0 g Ethylene Glycol
16.4 g Deionized Water
11.6 g NaOH (50% aqueous)
12.50 g Polyalkylated arylalkyl sulfonic acid from example 1
37.5 g Branched Monoalkylbenzene Sulfonic Acid Formulation B
17.0 g Isopropanol
5.0 g Ethylene Glycol
16.4 g Deionized Water
11.6 g NaOH (50% aqueous)
30.0 g Heavy alkyl benzene sulfonate, Commercial Source
20.0 g Branched Monoalkylbenzene Sulfonic Acid Formulation C
17.0 g Isopropanol
5.0 g Ethylene Glycol
16.4 g Deionized Water
11.6 g NaOH (50% aqueous)
10.0 g Polyalkylated arylalkyl sulfonic acid from example 9
40.0 g XSA-14

Each of the three surfactant formulations above was diluted to 0.3 wt % with synthetic field brine of the composition shown in Table 3. The alkalinity range used was from 0.6 to 1.40 wt % NaOH. The interfacial tension (IFT) of each sample was measured against a crude oil sample with API gravity of 24 at 45° C. using a Model 500 Interfacial Tensiometer from the University of Texas, Austin, Tex.

TABLE 3

| Synthetic Brine Formulation | |
|---|---|
| INGREDIENT | CONC. mg/L |
| $CO_3^{-2}$ | 375 |
| $HCO_3^-$ | 1342 |
| $Cl^-$ | 691 |
| $SO_4^{-2}$ | 4.8 |
| $Ca^{+2}$ | 16 |
| $Mg^{+2}$ | 7.3 |
| $Na^+$ | 1212 |
| Total Dissolved Solids | 3648 |

The results shown in Table 4 below indicate that the polyalkylated aryl alkyl sulfonates produced by the present invention gives ultra-low interfacial tensions comparable to and somewhat superior to the heavy alkylbenzene sulfonate, which is commercially available co-products. Formulation C has the additional advantage of using surfactants only derived from olefins and aromatics and not requiring sulfonates derived from alkylbenzene or heavy alkyl benzene such as the case with Formulation B.

TABLE 4

| Interfacial Tensions Against Crude Oil, 45° C. | | | |
|---|---|---|---|
| | IFT, mN/m | | |
| NaOH, wt, % | Formulation A | Formulation B | Formulation C |
| 0.6 | $8.5 \times 10^{-3}$ | $0.7 \times 10^{-3}$ | $5.2 \times 10^{-3}$ |
| 0.8 | $6.2 \times 10^{-3}$ | $6.5 \times 10^{-3}$ | $3.1 \times 10^{-3}$ |
| 1.0 | $3.8 \times 10^{-3}$ | $1.6 \times 10^{-2}$ | $2.1 \times 10^{-3}$ |
| 1.2 | $1.3 \times 10^{-3}$ | $4.3 \times 10^{-2}$ | $7.3 \times 10^{-3}$ |
| 1.4 | $6.6 \times 10^{-3}$ | $5.1 \times 10^{-2}$ | $2.5 \times 10^{-2}$ |

The invention and the manner and process of making and using it, are now described in such full, clear, concise and exact terms as to enable any person skilled in the art to which it pertains, to make and use same. It is to be understood that the foregoing describes preferred embodiments of the present invention and that modifications may be made therein depending from the spirit and scope of the present invention as set forth in the claims.

The invention claimed is:

1. A process for the manufacture of polyalkylated arylalkyl sulfonic acids and their salts comprising: reacting a sulfonated aryl alkylaromatic compound of the structure below:

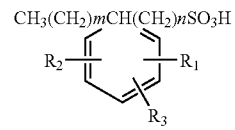

Where
$R_1$, $R_2$ and $R_3$ are each separately and independently H, alkyl (branched or linear C1 to C30), ($—CH_2CH_2O)_aH$, ($—CH(CH_3)CH_2O)_bH$, or ($—CH_2CH_2O)_c(—CH_2(CH_3)CH_2O)_dH$,
m+n=8 to 28
a=1 to 30
b=1 to 30
c+d=2 to 30
with one or more olefin to form the polyalkylated arylalkyl sulfonic acid structure below:

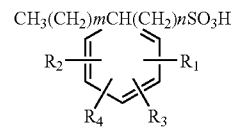

Where
$R_1$, $R_2$ and $R_3$ are each separately and independently H, alkyl (branched or linear C1 to C30), ($—CH_2CH_2O)_aH$, ($—CH(CH_3)CH_2O)_bH$, or ($—CH_2CH_2O)_c(—CH_2(CH_3)CH_2O)_dH$,
m+n=8 to 28
$R_4=CH_2CH_3$, $CH_2CH_2Y$ or $Y(CH_2)_pCH(CH_2)_qY$
p+q=0 to 27
a=1 to 30
b=1 to 30
c+d=2 to 30
Y=$CH_3$, COOH, $CH_2OH$, $CH_2(—CH_2CH_2O)_aH$, $CH_2(—CH(CH_3)CH_2O)_bH$, $CH_2(—CH_2CH_2O)_c(—CH_2(Ch_3)Ch_2O)_dH$, aromatic, or substituted aro{yt}matic.

2. The process for the manufacture of polyalkylated arylalkyl sulfonlo acids and their salts of claim 1 where the olefin is an alpha olefin having 2 to 30 carbons.

3. The process far the manufacture of polyalkylated arylalkyl suifonic acids and their salts of claim 1 where the olefin is an internal olefin having 4 to 30 carbons.

4. The process for the manufacture of polyalkylated arylalkyl sulfonic acids and their salts of claim 1 where the reaction is carried out at temperatures between 400° C. and 200° C.

5. The process far the manufacture of polyalkylated arylalkyl sulfonic acids and their salts of claim 1 where the reaction is carried out at atmospheric pressures.

6. The process for the manufacture of polyalkylated arylalkyl sulfonic acids of claim 1 where the reaction is carried out at elevated pressures.

7. The process far the manufacture of polyalkylated arylalkyl sulfonic acids and their salts of claim 1 where the olefin is terminated by one or more carboxylate groups.

8. The process for the manufacture of polyalkylated arylalkyl sulfonic acids and their salts of claim 1 where the olefin is terminated by one or more alcohol groups.

9. The process for the manufacture of polyalkylated arylalkyl sulfonic acids end their salts of claim 1 where the olefin is terminated by one or more benzene groups.

10. The process for the manufacture of polyalkylated arylalkyl sulfonic acids and their salts of claim 1 where the olefin is terminated by one or more substituted aromatic groups.

11. The process for the manufacture of polyalkylated arylalkyl sulfonic acids and their salts of claim 1 where the olefin may be terminated with one or more groups chosen from: carboxylate, alcohol, benzene, substituted benzene.

12. The process for the manufacture of polyalkylated arylalkyl sulfonic acids and their salts of claim 1 where the polyalkylated aryl alkyl sulfonic acid formed is neutralized with an alkali.

13. The process for the manufacture of polyalkylated arylalkyl sulfonic acids and their salts of claim 1 where the polyalkylated aryl alkyl sulfonic acid formed is neutralized with an alkali selected from the group: sodium hydroxide, sodium carbonate, potassium hydroxide, potassium carbonate, calcium hydroxide, magnesium hydroxide, ammonium hydroxide, amine.

* * * * *